United States Patent [19]
Iino et al.

[11] Patent Number: 5,119,026
[45] Date of Patent: Jun. 2, 1992

[54] MAGNETIC RESONANCE IMAGING APPARATUS

[75] Inventors: Mitsutoshi Iino; Shirou Nakatao, both of Hino; Hiromi Kawaguchi, Kawasaki; Masaru Tanaka; Toshiaki Yonekura, both of Hino, all of Japan

[73] Assignees: Fuji Electric Co., Ltd., Kawasaki; Fujifacom Corporation, Hino, both of Japan

[21] Appl. No.: 460,112

[22] Filed: May 3, 1990

[30] Foreign Application Priority Data

Sep. 9, 1988 [JP] Japan ................... 63-224406

[51] Int. Cl.$^5$ ........................................ G01R 33/20
[52] U.S. Cl. ........................................ 324/309
[58] Field of Search ............ 324/300, 307, 309, 310, 324/311, 312, 313, 314, 318, 322; 128/653 A, 653 AF

[56] References Cited

U.S. PATENT DOCUMENTS 4,796,635  1/1989  Dumoulin ................ 128/653 AF

OTHER PUBLICATIONS

"NMR Fourier Zeugmatography", Kumar et al. Journal of Magnetic Resonance 18, 69–83, 1975.
"A Parallel Algorithm for Rotating-Frame Zeugmatography", Chen et al., Magnetic Resonance in Medicine 1, 354–360, 1984.

Primary Examiner—Michael J. Tokar
Attorney, Agent, or Firm—Spencer, Frank & Schneider

[57] ABSTRACT

An arrangement in a magnetic resonance imaging apparatus for producing image data of an object being examined. The object is subjected to magnetic fields and RF pulse signals which produce echo signals. The echo signals which represent views of the object are detected. Data collecting circuitry selectively performs a data collection process on the detected echo signals to produce collected data such that, for those echo signals of a relatively small strength, part of the data collection process is suppressed and, for those echo signals of a relatively great strength, the data collection process is performed a plurality of times under identical operating conditions. A data processor processes the collected data to produce view data such that, for the echo signals for which the data collection process has been suppressed, interpolation data is produced and, for the echo signals for which the data collection process has been performed a plurality of times, a summing and averaging operation is performed on the collected data. The data processor combines the interpolation data with the summed and averaged data thereby producing view data. An image constructor performs a Fourier transform on the view data thereby constructing image data.

18 Claims, 13 Drawing Sheets

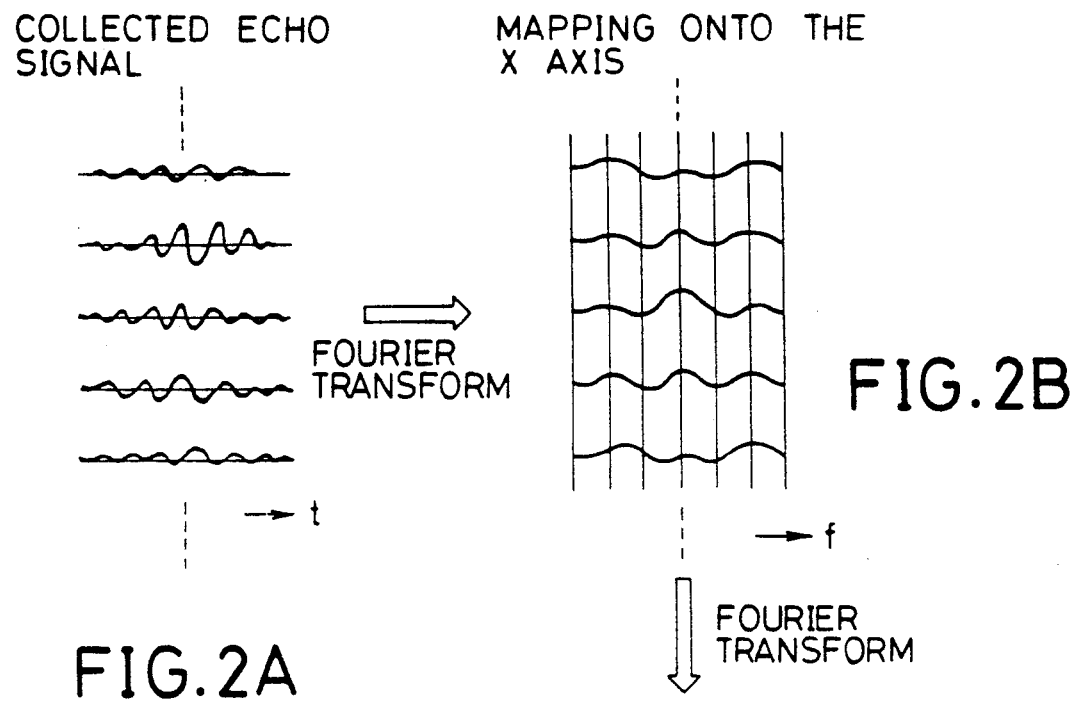
FIG.2A
FIG.2B
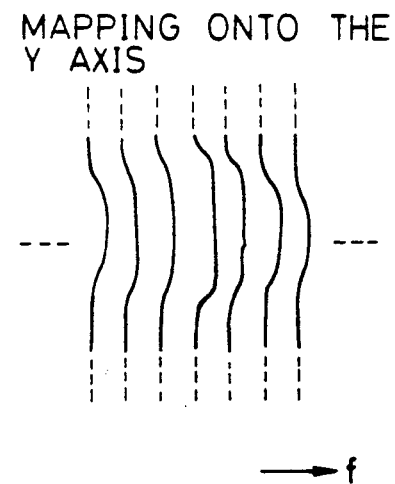
FIG.2C

MAGNETIC RESONANCE IMAGING APPARATUS

TECHNICAL FIELD

The present invention relates to a magnetic resonance imaging apparatus that employs the Fourier transform technique.

BACKGROUND ART

The magnetic resonance imaging provides images such as those of plane sections of a body, by making use of the property of a certain atom or nucleus (such as a hydrogen atom or nucleus) which exhibits a magnetic resonance phenomenon when it is placed in a uniform static magnetic field, causing its spin to have a precession about the static magnetic field, and when a radio frequency pulse (RF pulse) having the same frequency as that of the precession is applied to the body in that state. Magnetic resonance imaging employing the Fourier transform technique superimposes gradient magnetic fields $G_x$, $G_y$, and $G_z$ over the static magnetic field, the gradient magnetic fields having their strengths varying along the three axes consisting of the X axis, Y axis and Z axis. This allows each individual atom or nucleus in an object to undergo a magnetic resonance or relaxation with the frequency that varies with the varying strengths of the magnetic fields $G_x$, $G_y$, $G_z$. The frequency of the echo signal that results from the magnetic resonance or relaxation is then analyzed by employing the Fourier transform, and an image is provided.

The typical pulse sequence which may be used in the magnetic resonance imaging that employs the Fourier transform is presented in FIG. 1. As can be seen from FIG. 1, the 90° RF pulse 11 whose amplitude is maodulated with a 21-MFz carrier, and the gradient magnetic field $G_z$ 13 along the Z axis are intended to enable a selective excitation of the plane sections which are perpendicular to the Z axis. The 180° RF pulse 12 and the gradient magnetic field $G_x$ 14 along the X axis are intended to provide a signal that results from the excited spin in the form of an echo signal 16. The echo signal 16 at that point in time contains a frequency component which depends upon the distribution of the spin along the X axis within a particular plane section, and this distribution of the spin along the X axis is encoded in the form of the frequency of the echo signal (frequency encoding). Moreover, the gradient magnetic field $G_y$ 15 which extends along the Y axis orthogonally to each of the two gradient magnetic fields $G_z$ and $G_x$ has its magnitude value shifted from the positive to negative (or vice versa) sequentially each time one echo signal (view) is collected. This causes the amount of the phase encoding to change accordingly which allows the distribution of the spin along the Y axis within the plane section to be encoded in the form of the phase of the echo signal (phase encoding).

The described magnetic resonance imaging that employs the Fourier transform is currently available in various types, some of which are named as follows:

(1) Fourier Zeugmatography (Original Method)

It is described in "NMR Fourier Zeugmatography" by Kumar. A, Welti. D & Ernst R., J. Magn. Reson, 18, p.69 (1975).

(2) Spin Warp Technique

It is described in "Spin Warp NMR Imaging and Applications to Human Whole-Body Imaging" by Edelstein W. A, Hutchison J. M. S. Johnson G & Redpath T. W., Phys, Med. Biol., 25, p.751 (1980). This technique uses the field echoing method as the mechanism to produce the echo signal, and provides the same mathematical solutions that are found in (1) above.

(3) Improved Spin Warp the example shown in FIG. 2).

It is specifically intended to produce echoes by using 180° RF pulses. In other aspects, its principle is the same as for preceding methods (1) and (2).

(4) Half Phase Encoding

It uses the principle of any one of the preceding methods (1), (2) and (3), or the combination of those methods. It may be distinguished from the other methods in that this method uses the part of the signal in which the strength is great (which is equal to half the whole) while discarding the remaining half that may deteriorate the S/N ratio for the signal.

(5) $\frac{2}{3}$ Phase Encoding

It is essentially based on the same concept as for the method (4), and provides a S/N ratio and spatial resolution that are intermediate between any two of the methods (1), (2), and (3).

(5) Weighting Projection Method (as disclosed in Patent Application No. 62-46243).

This is an expanded version of the preceding methods (4) or (5), whereby a statistical weight is given such that the number of cumulative calculations is increased for the part of the signal in which its strength has some significance, and is decreased for the part which may deteriorate the S/N ratio. This allows for selective improvement of the S/N ratio.

The NMR signals that have thus been collected are very weak signals, and it is therefore generally the case that the collection of the NMR signals occur several times and the cumulative calculations are performed on those NMR signals under identical encoding conditions. The S/N ratio may be improved in this way. In all of the methods (1) to (5) described above, the cumulative calculations on the signals may cause the data collection time to increase in proportion to the number of calculations to be performed. For the weighting projection method (6), the data collection time might increase as compared with the case where no cumulative calculations occur.

Generally, data collection time accounts for the major part of the time required for examination by a magnetic resonance imaging apparatus, and any increase in the data collection time would lead to increasing the examination time accordingly, which might cause a reduction in the examination efficiency, and in some cases where the particular object to be examined is a human body or patient, would cause additional pain to the patient.

SUMMARY OR THE INVENTION

It is accordingly an object of the present invention to provide a magnetic resonance imaging apparatus that can improve the S/N ratio for any resulting images without the need of increasing the data collection time.

In achieving the above object, the present invention may include means for detecting views in the form of echo signals from a particular object being examined, data collecting means that suppresses part of the data collection for some of the detected views whose signals have a relatively small strength, and performs the data collection several times under the identical conditions for the other detected views whose signals have a relatively great strength, data processing means that creates data which will be interpolated between the data for the individual views for which the data collection has been suppressed, and sums the data for the individual views for which the data collection has occurred several times to provide an average view data, and image reconstruct means that provides the Fourier transform functions for the view data provided by the data processing means and creates the corresponding image data.

It is noted here that the gradient magnetic field for the phase encoding may be varied a particular number of times, and the appropriate views may be obtained by detecting the corresponding number of echo signals. Then, the data collection may be suppressed for some of those views for which the amount of phase encoding is relatively great, and the data collection may occur several times in the same phase encoding gradient magnetic field for other views for which the amount of phase encoding is relatively small. The pattern used to vary the phase encoding gradient magnetic field may be prestored in any suitable memory.

A memory may be provided which is evenly divided into two regions, and all of the individual view data that has been collected by the data collecting means may also be evenly divided into two sections. Then, the individual view data in each section may be arranged in the memory layout, beginning with the border line between the two memory regions toward the uppermost address and toward the lowermost address, and may be stored in the respective regions in the memory.

In its specific form, the data collecting means may comprise a scan controller.

In its specific form, the data processing means may be implemented by an array processor which contains a data memory which may be evenly divided into two regions. The collection of all the individual view data collected by the data collecting means may be evenly divided into two sections, and may be arranged in the memory layout and stored in the respective regions, beginning with the border line between the two memory regions toward the uppermost address and toward the lowermost address.

BRIEF DESCRIPTION OF THE DRAWINGS

FIGS. 1A, 2B, and 2C are schematic illustrations to help understand the operation in general of the Fourier transform;

DETAILED DESCRIPTION OF THE PREFERRED EMBODIMENTS

The Fourier transform technique consists essentially of varying the phase encoding gradient magnetic field (see the magnetic field Gy 15 FIG. 1) so that a certain phase difference may occur in echo signals when the phase encoding is performed. This phase difference may occur in proportion to the time integral of the gradient magnetic field Gy (which appears as an area on the sequence chart). Generally, if an image containing $256 \times 256$ picture elements is to be produced, for example, 256 echo signals (views) would be collected as a result of varying the phase encoding gradient magnetic field Gy as many times as 256.

It is then supposed, for example, that the echo signals have been collected as shown in FIG. 2A. If an image is to be created (reconstructed) from those collected echo signals, the Fourier transform is first performed for each individual view. This produces a frequency component for the signal. As the frequency component for each echo signal depends upon the distribution of the spin along the X axis within a particular plane section, the information on the spin at every point within the plane section will be mapped onto the X axis as shown in 2B.

When the Fourier transform is then performed on a collection of the points where any views have the identical frequency, the spin information at each of those points may be mapped onto the Y axis as shown in FIG. 2C. Finally, the spin information at every point within the plane section will be mapped onto the image.

Figure 3:
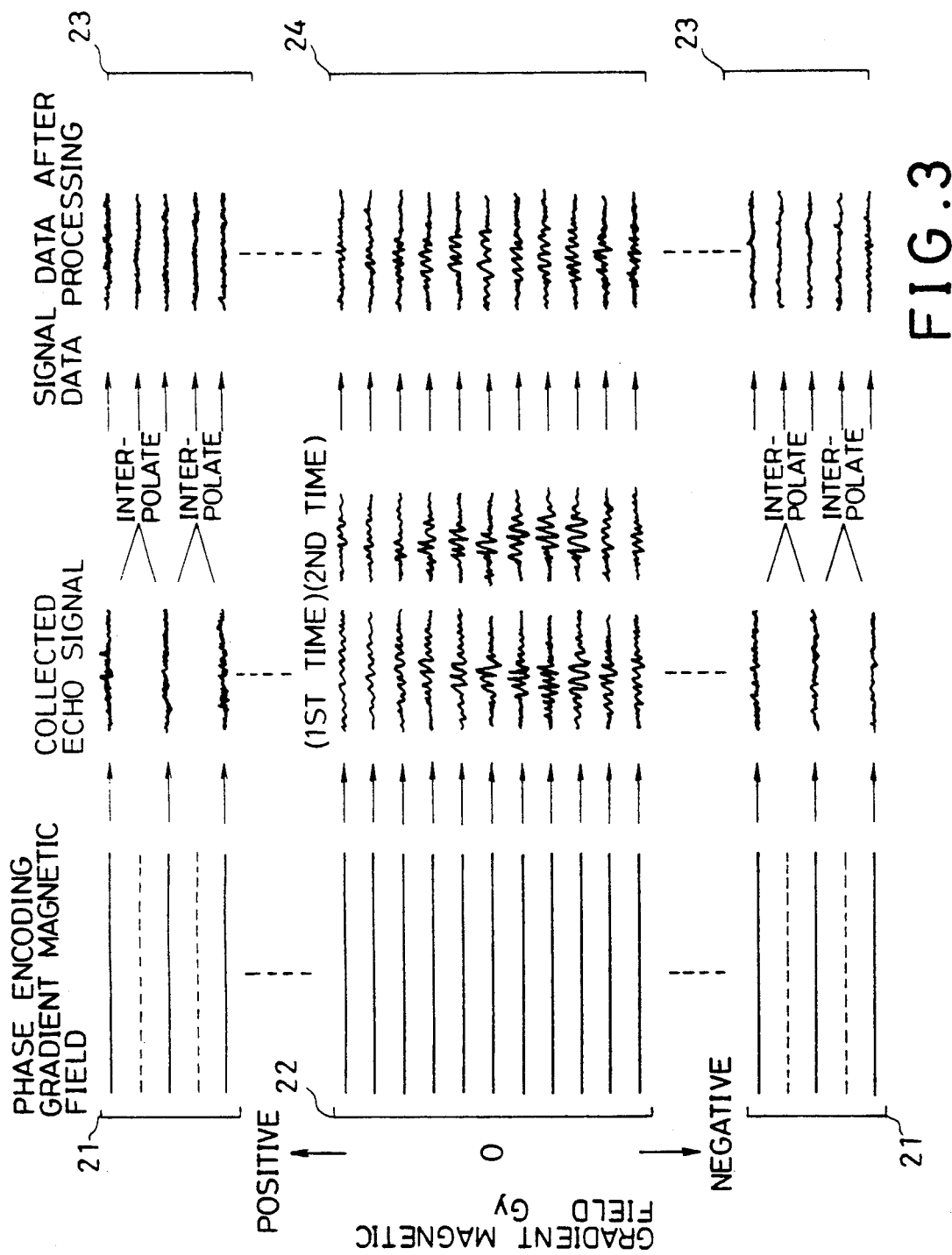
FIG. 3 is a schematic illustration to help understand the basic concept of the present invention whereby the data collection may occur variably depending on the amount of phase encoding, in response to any variation in the phase encoding gradient magnetic field.

As may be seen from the example in FIG. 3, according to the present invention, the data collection will be suppressed for those views 21 for which the amount of phase encoding is relatively great, and the data collection will occur several times in the identical phase encoding magnetic field for those views 22 located near the center. For those views for which the data collection is suppressed, any suitable linear interpolation or like technique may then be used to produce the interpolated signal data 23. For the views for which the data collecting has occurred several times, the summing and averaging operation may then be performed to provide the signal data 24 whose S/N ratio has been improved.

As determined by the nature of the Fourier transform, those views located in the center for which the summing and averaging operation is to be performed correspond to the low frequency component in the image, and those views located in the periphery for which the interpolation is to be performed correspond to the high frequency component in the image. As such, the present invention provides the higher signal accuracy of the low frequency component in the image, and provides an improved S/N ratio improving the quality of the image. In the magnetic resonance imaging, in general, the low frequency component in the image has a contrast resolution (low contrast resolution) that may have a large effect upon the quality of the image. In this respect, the present invention has a significant effect.

The strength of the echo signal that will be obtained may be expressed by the equation as follows:

$$S(t,Gy) = \int\int \rho(x,y) \cdot \exp(ir\int Gxdt \cdot x + ir\int Gydt \cdot y) dx dy$$

where
S(t,Gy): the strength of the echo signal
$\rho(x,y)$: the spin density distribution within a plane section
Gx: the gradient magnetic field slope along the X axis
Gy: the gradient magnetic field slope along the Y axis
t: time
k: constant
r: magnetic resonance ratio
i: $(-1)^{\frac{1}{2}}$ As it may be seen from the above equation, the echo signal will have its maximum value when the conditions of $\int Gxdt \rightarrow 0$ and $\int Gydt \rightarrow 0$ are met. Incidentally, in the present invention, few signals will yield a large value of time integral $\int Gydt$ of the phase encoding gradient magnetic field. Furthermore, because the values of time integrals at portions of the data interpolation are small, the deterioration of the signal accuracy involved in the data interpolation will have little effect on the image quality.

Figure 4:
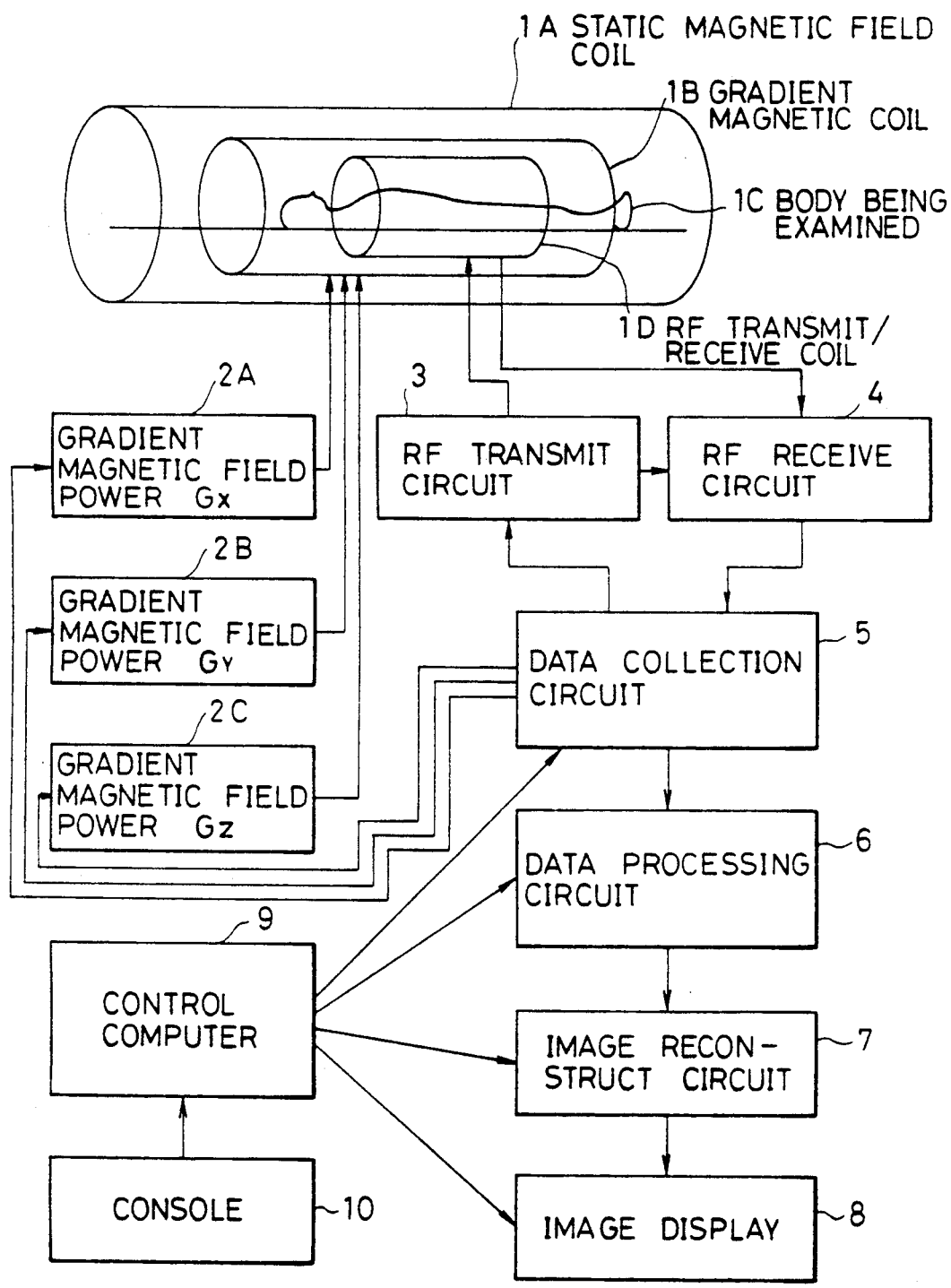
FIG. 4 is a block diagram showing one preferred embodiment of the present invention.

FIG. 4 is a block diagram showing one embodiment of the present invention. In FIG. 4, there are a static magnetic field coil 1A that produces a uniform static magnetic field, a gradient magnetic field coil 1B that is disposed inside the coil 1A and produces each of the gradient magnetic fields Gx, Gy, and Gz, and an RF coil 1D that is adapted to receive and transmit an RF magnetic field. The RF coil 1D is located inside the coil 1B. Those coils 1A, 1B and 1D are placed so as to surround a human body 1C being examined. There are also power sources 2A, 2B and 2C for the gradient fields, which control the corresponding gradient magnetic field Gx, Gy, and Gz along the X, Y and Z axes. An RF transmit circuit 3 delivers a RF pulse to be applied to the coil 1D, and the echo signal that is produced from the object 1C is detected by the coil 1D. An RF receive circuit 4 receives this detected signal. A data collection circuit 5 is adapted to collect the echo signals from the RF receive circuit 4 in the manner as described in FIG. 3. In the data collection circuit 5, part of the data collection is suppressed for the views whose signal strengths are relatively small, and the data collection occurs several times under the same conditions for the views whose signal strengths are relatively great. A data processing circuit 6 uses the data collected by the data collecting circuit 5 to create the appropriate data when the interpolation process occurs for the views for which the data collection has been suppressed. For the views for which the data collection has occurred several times, this circuit 6 provides NMR data by summing the collected data and taking the average thereof. An image reconstruct circuit 7 is provided for creating the appropriate image data, based on the NMR data from the data processing circuit 6. An image display 8 presents the appropriate image from the image reconstruct circuit 7. A computer 9 provides control and supervisory functions over the total system, and a console device 10 allows the operator to enter instructions or commands and data into the computer 9.

Referring next to FIG. 4, the operation is described below.

In response to a camera start command entered from the console 10, the controlling computer 9, passes parameters specifying the matrix size, the thickness of a plane section, and so on, to the data collection circuit 5. When the data collection circuit 5 receives those parameters, it controls the gradient magnetic field power sources 2A, 2B and 2C, the RF transit circuit 3 and RF receive circuit 4 as specified by the parameters and in the pulse sequences such as the ones shown in FIG. 1, and collects echo signals issued from the body 1C through the RF receive coil 1D and RF receive circuit 4.

Figure 5:
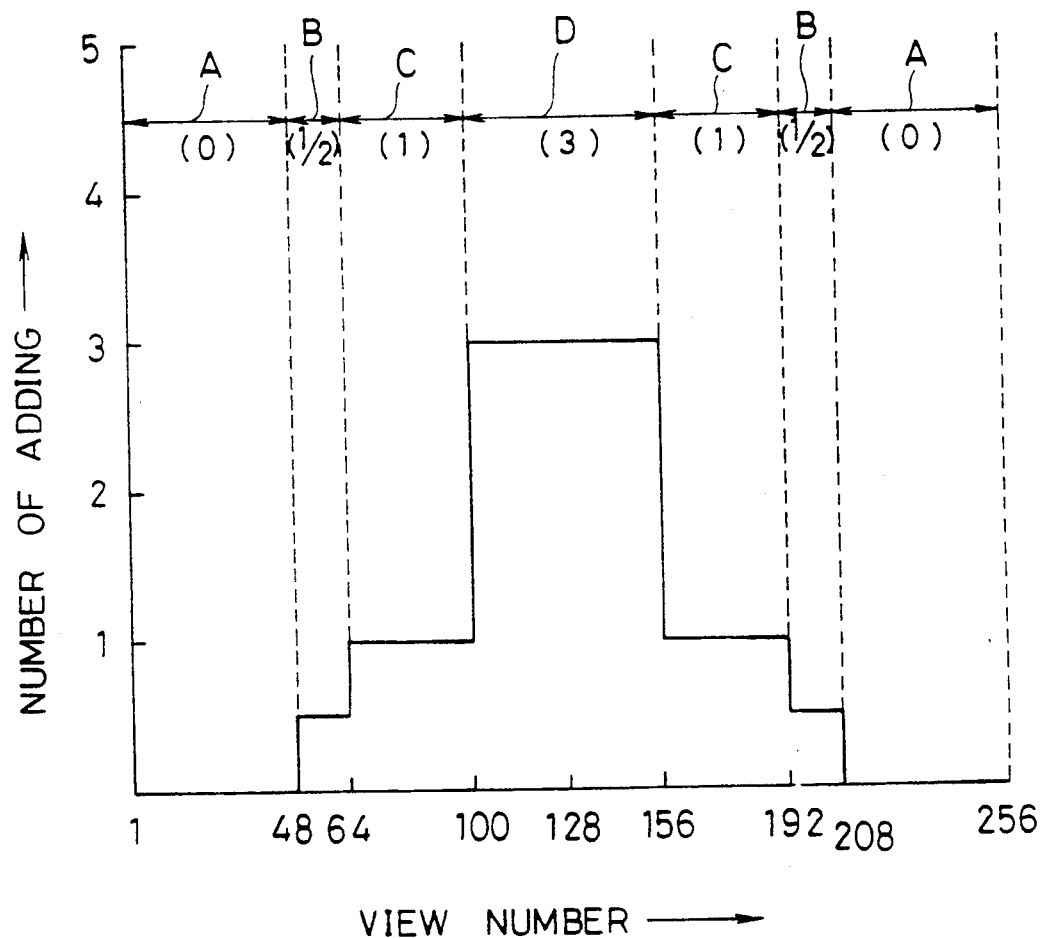
FIG. 5 is a schematic illustration to help understand a particular pattern example of the view data collection that may occur according to the present invention.

At this time, the data collection circuit 5 uses a varying pattern of the phase encoding gradient magnetic field such as the one shown in FIG. 5 to control the gradient magnetic field for the phase encoding. In the graphical chart in FIG. 5, the numbers of the collected individual view data are given along the abscissa (X axis), and the number of calculations (or count of collections if data collection occurs) is given along the ordinate (Y axis). As seen from FIG. 5, no data collection occurs for the region A, and the data collection occurs for every second view data in the region B. For the region C, the data collection occurs a single time under the same phase encoding conditions, and for the region D, the data collection occurs three times under the same phase encoding conditions. As a result, the total number of the views for which the data collection has occurred amounts to 256, which is equal to the number of views for which the summing/averaging operation and data interpolation operation have not occurred.

The data that has been collected as above is transferred to the data processing circuit 6, which performs the data interpolation operation and summing/averaging operation on the data as required such as in the example of FIG. 5. In FIG. 5, the region A will have the interpolation value of 0, and the region B will have linear interpolation. The data in the region C will be provided as it is unprocessed, and the data in the region D will be subjected to a summing/averaging operation. Following those data collection steps, the image reconstruct circuit 7 provides appropriate image data, from which the image is displayed on the image display 8.

It should be understood that the interpolation functions may include sin x/x interpolation and spline function interpolation instead of the linear interpolation mentioned above.

When an image is created from the collected view data pattern such as the one shown in FIG. 5, the S/N ratio for the image may be improved by a factor of 1.3 to 1.4, as compared with that for the prior art, which has been demonstrated by experimentation.

The data collection circuit 5 described above may be included as part of a scan controller which may be controlled by controlling computer 9 that provides a scanning CPU.

Figure 6:
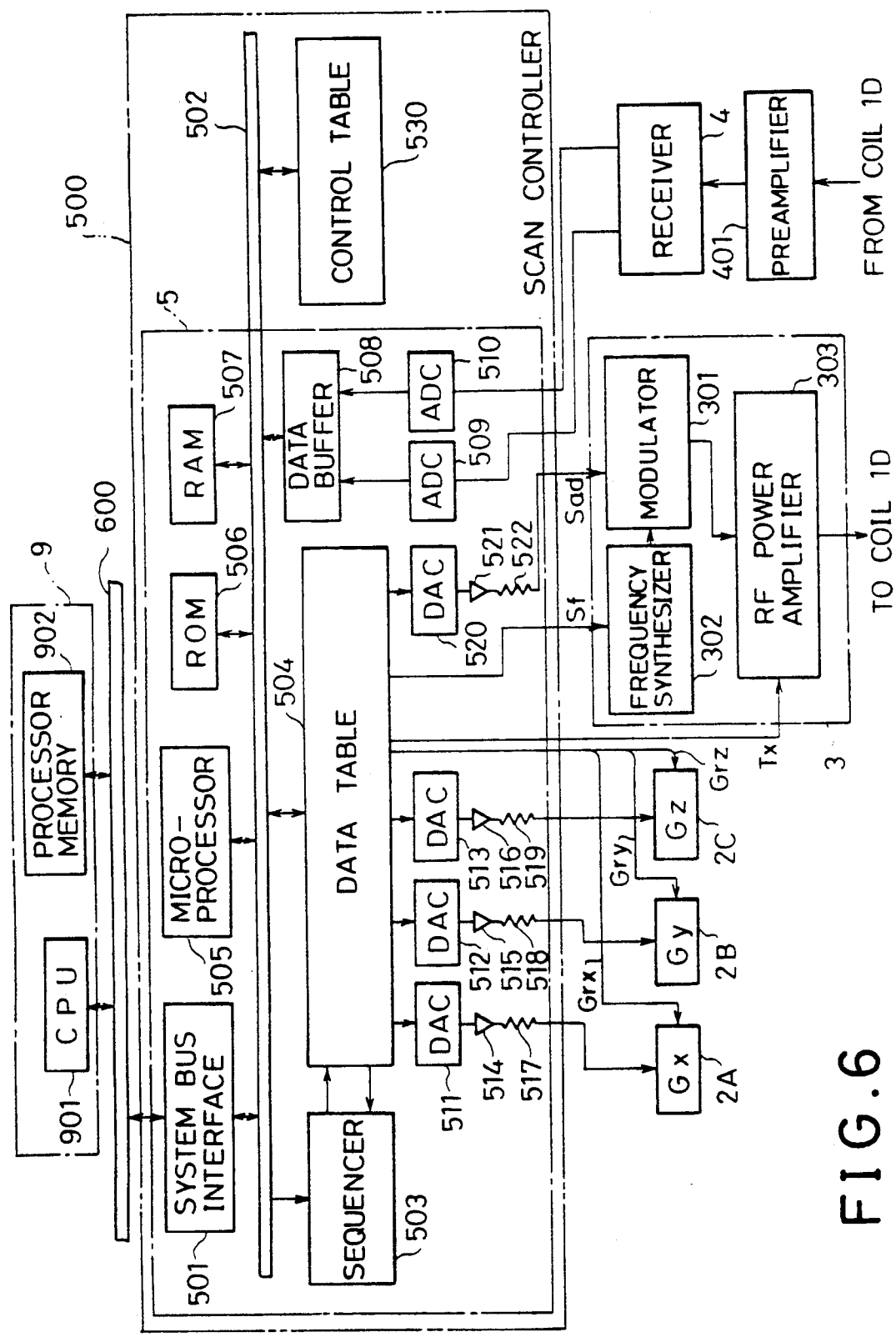
FIG. 6 is a block diagram showing a specific embodiment of the data collector circuit 5 shown in FIG. 4.

Referring to FIG. 6, there is a scanning CPU bus 600 on which data is transferred between the controlling computer 9 and scan controller 500. The scan controller 500 includes a system bus interface 501 which connects between the scanning CPU bus 600 and a scan controller bus 502, a sequency controller 503 (referred simply to as "sequencer"), and a 256K RAM 504 that contains as a data table sequence data including wave data representing each respective wave as identified by 11, ..., 15 in FIG. 1 in digital form, wave transit timing, data sampling timing, and termination interrupted transmit timing. The sequencer 503 writes and reads the data to and from the data table 504 under control of a microprocessor 505. The microprocessor 505 communicates with ROM 506 which stores the control program for the microprocessor, and RAM 507 which temporarily stores any processed data. A data buffer 508 receives the echo signals from the receive circuit 4 through A/D converters 509 and 510.

The digital data for the waves 14, 15 and 13 specified in the data table 504 is transferred to respective D/A converters 511, 512, and 513 which provide respective corresponding analog data. Each analog data is then delivered to respective buffer amplifiers 514, 515 and 516 and then through respective resistors 517, 518, and 519, going to the respective Gx, Gy, and Gz power sources 2A, 2B and 2C which are then energized. Enable signals Grx, Gry, and Grz are also fed to those power sources 2A, 2B and 2C from the data table 504. The digital data for the RF wave, which is retrieved from the data table 504, is fed to a D/A converter 520 which provides the corresponding analog data Sad which goes to a modulator circuit 301 forming the transmit circuit 3 through a buffer amplifier 521 and then a resistor 522. A frequency synthesizer 302 allows the modulation frequency to be set to any particular value. This modulation frequency may be set by the appropriate frequency setting signal Sf from the data table 504. The modulated output from the modulation circuit 301 is fed to an RF power amplifier 303 which provides an RF output to be fed to the RF receive and transmit coil 1D. Then, a transmit enable signal Tx, which determines the timing at which the wave is to be sent from the data table 504, is fed to the coil 1D. The RF output will only be fed to the coil 1D when this signal Tx is available.

The echo signal in the form of the RF signal, as detected by the coil 1D, is delivered to the receive circuit 4 through a preamplifier 401. In the receive circuit 4, the echo signal is demodulated from the input RF signal, transferred to the A/D converters 509 and 510 and is temporarily stored in the data buffer 508.

A control table which is identified 530 is provided to contain the control data which may be used to control the transmit circuit 3, the receive circuit 4, the positioning of the bed for the body 1C being examined, and the various types of status information to be displayed.

In FIG. 6, the controlling computer 9 contains a CPU 901 and a processor memory 902. The processor memory 902 stores a phase encoding control table later to be described.

Figure 7:
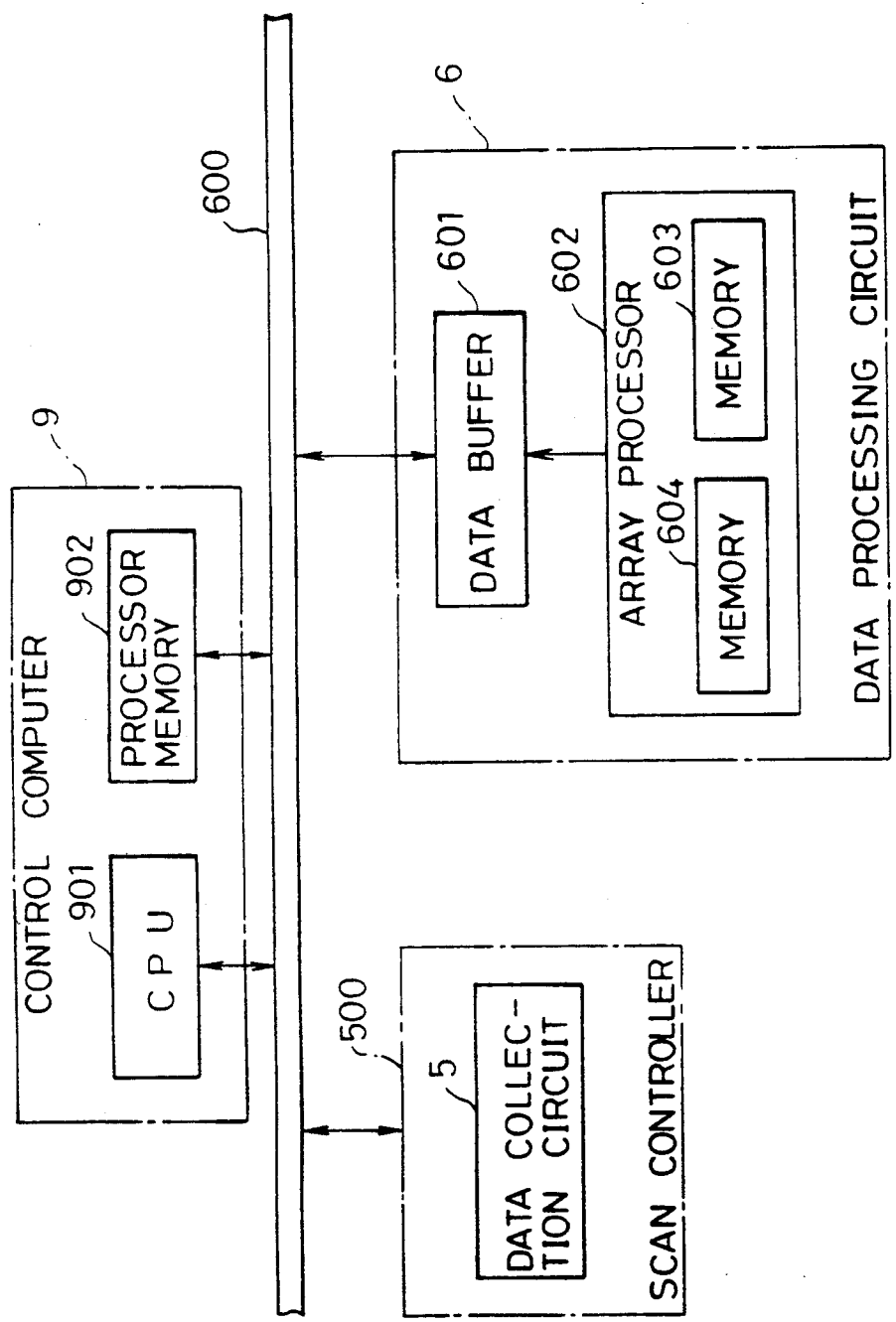
FIG. 7 is a block diagram showing a specific embodiment of the data processing circuit 6 shown in FIG. 4.

FIG. 7 illustrates one example of the data processing circuit 6 which contains a data buffer 601 which receives and sends data from and to the scanning CPU bus 600. An array processor 602 is implemented as an arithmetic processor, which contains a 4MB RAM 603 which provides the data memory and a program memory 604 in which the algorithms written to perform the summing/averaging and interpolation operations reside. The data memory or RAM 603 contains a table that is used to control the summing/averaging and interpolation functions, which will later be described.

Referring back to FIG. 5, the two control data tables will be described for the collected data pattern. As the preliminary steps, those table are prepared as follows.

(1) Phase Encoding Control Table

This table is created in the CPU processor memory 902, including the gradient magnetic field output values for the phase encoding. In the example shown in FIG. 5, the pattern has a 256×256 matrix, and the table must have the corresponding number of entries (256). This phase encoding control table is also required for the usual pattern (for which the count of summing is 1 for all views). For the usual pattern, suppose that the phase encoding output value is incremented by +1 between −128 and +127, then the resulting phase encoding control table for the collected data pattern will look like the one shown in FIG. 8. More specifically, the data output value will be incremented by +2 between −80 and −66, and will be incremented by +1 between −64 and −29. Between −28 and +27, the data output value will be incremented by +1 each time and after three identical values appear. The data output value will be incremented by +1 between 28 and 63, and will be incremented by +2 between 65 and 79.

(2) Summing/Averaging and Interpolation Control Table

This table is created in the array processor memory 603, including the control pattern for the summing/averaging and interpolation algorithms. The table has a fixed number of entries, which include six entries such as the number of interpolated data views (0 value or extrapolated value), the number of ½ added views (interpolation of two-point data between two sampling points), the number of single added views (no summing/averaging and interpolation), the number of double added views (summing/averaging of the two-point data), and the number of triple added views (summing/averaging of the three-point data). The number of data views will be set equal to half (½) the actual number of views, for the convenience of the required calculation which will be described later. The number of views for each entry in sample pattern in FIG. 5 is given in the table 1 below.

TABLE 1

| Entry | Number of Views |
|---|---|
| Interpolated data view number | 48 |
| ⅓ added view number | 0 |
| ⅔ added view number | 8 |
| single added view number | 36 |
| double added view number | 0 |
| triple added view number | 28 |

Figure 9:
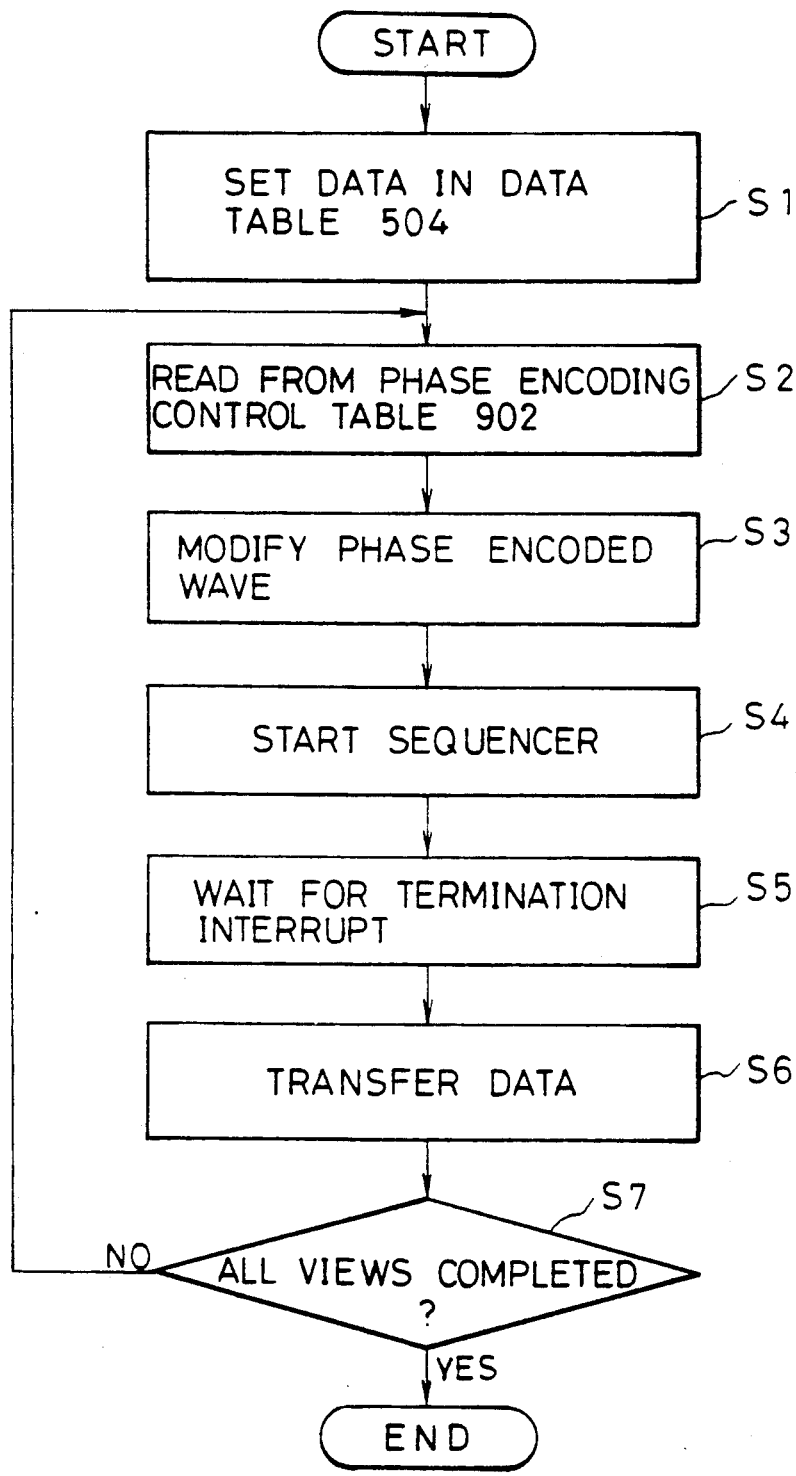
FIG. 9 is a flowchart showing one example of the data collection procedure.

One example of a data collecting procedure stored in ROM 506 in data collection circuit 5 is shown in FIG. 9.

Figure 1:
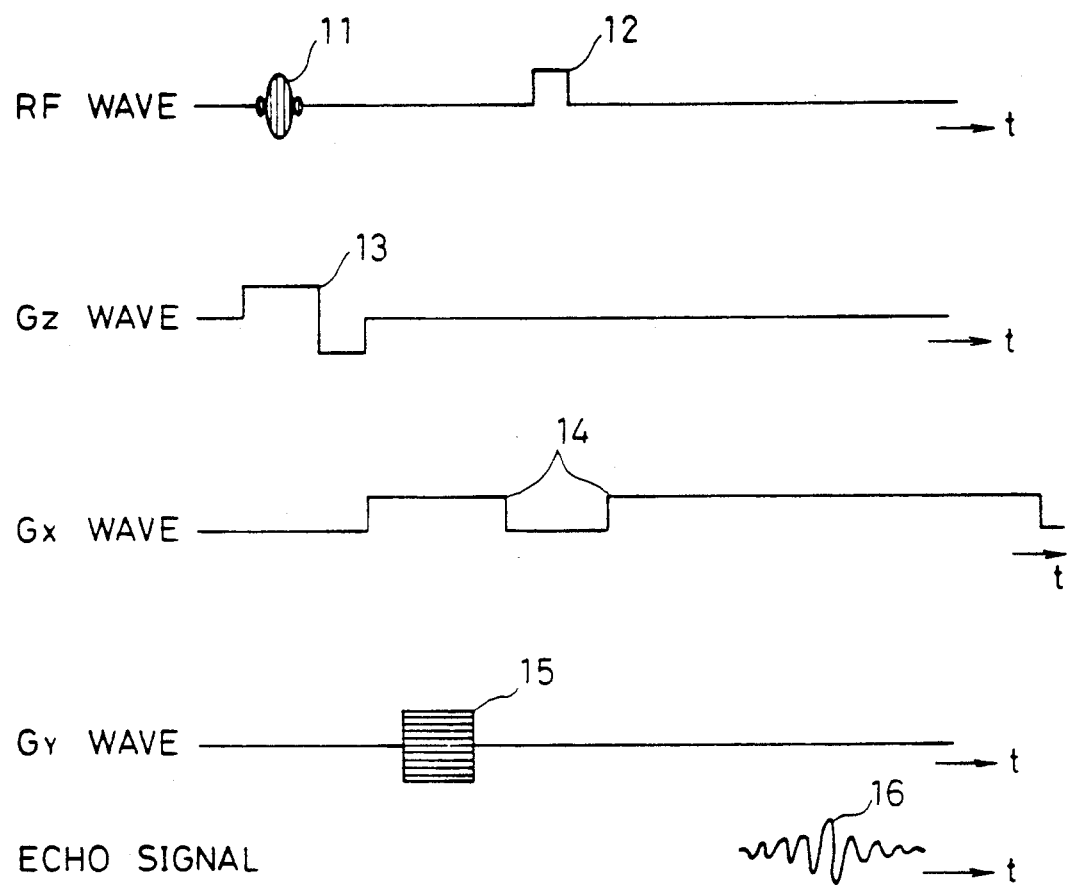
FIG. 1 is a timing chart showing the typical pulse sequence to be used in the Fourier transform.

At step S1, the sequence data that includes the wave data representing the waves 11, 15 in FIG. 1 in digital form, the wave transmit timing, the data sampling timing, and the termination interrupted transmit timing is set in the data table 504.

Figure 8:
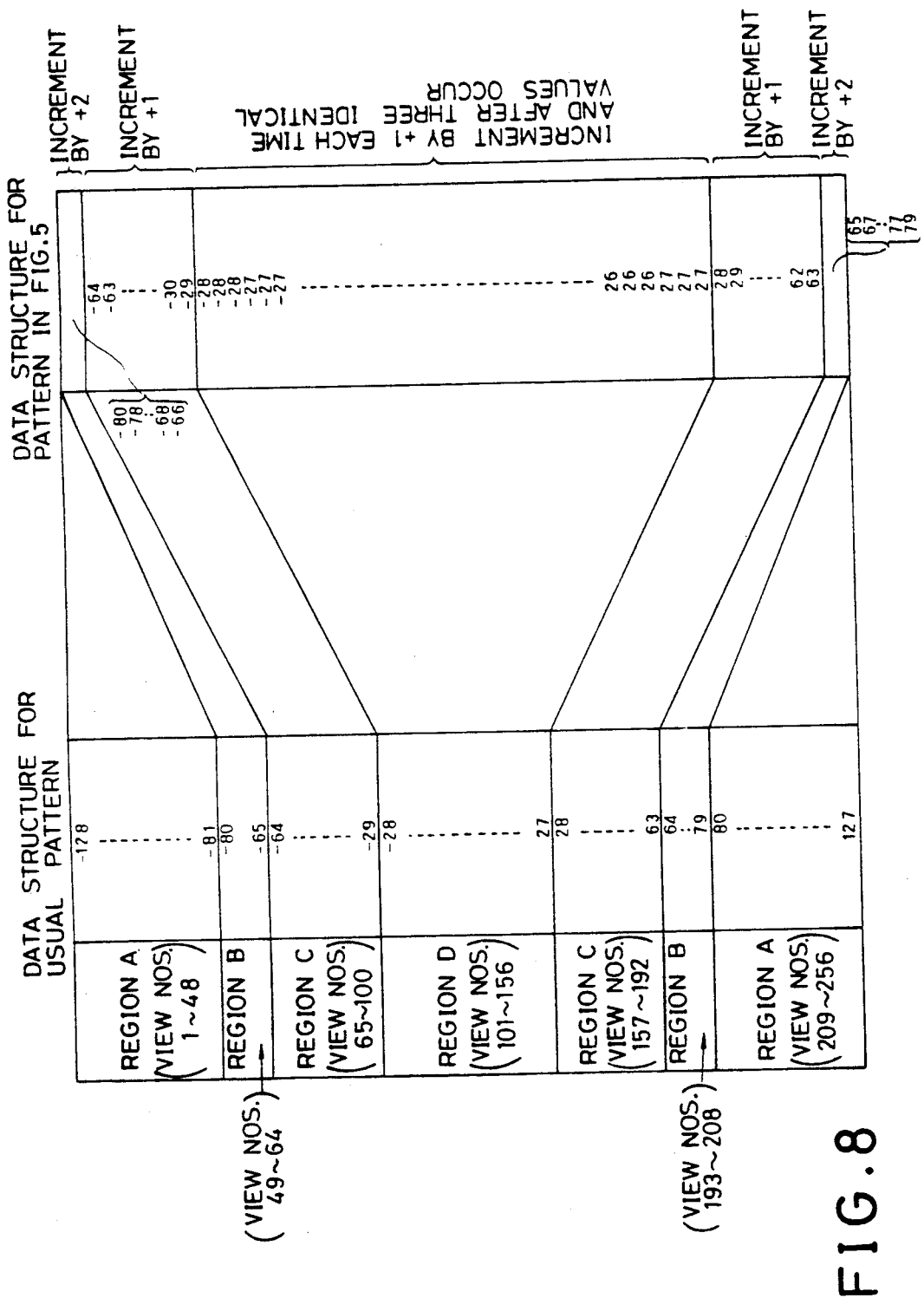
FIG. 8 is a schematic illustration to help understand one example of the phase encoding control table for the pattern example shown in FIG. 5.

At the following step S2, the data in FIG. 8 is read from the phase encoding control table 902. The table entries are moved one by one for each loop. At step S3, the phase encoded wave in the data table 504 is modified by the data read at the stp S2. In this way, the phase encoded wave 15 is modified like the wave 15 in FIG. 1.

At step S4, the sequencer 503 is started up. When the sequencer 503 is operational, it provides the RF pulse 11 to the transmit/receive coil 1D which delivers an echo signal to be stored in the data buffer 508.

At step S5, the sequencer 503 is placed in the wait state until it receives a data collection end interruption for one view from the data collection circuit 5. When the data collection for that view is completed, the interruption is caused, going to the following step S6. At step S6, the data is transferred from the data buffer 508 to the memory 603 in the array processor 602.

At step S7, it is determined whether all of the preceding steps S2 through S6 have been completed for all views. Those steps S2 through S6 will be repeated until the data collection for all views have been completed.

Figure 10:
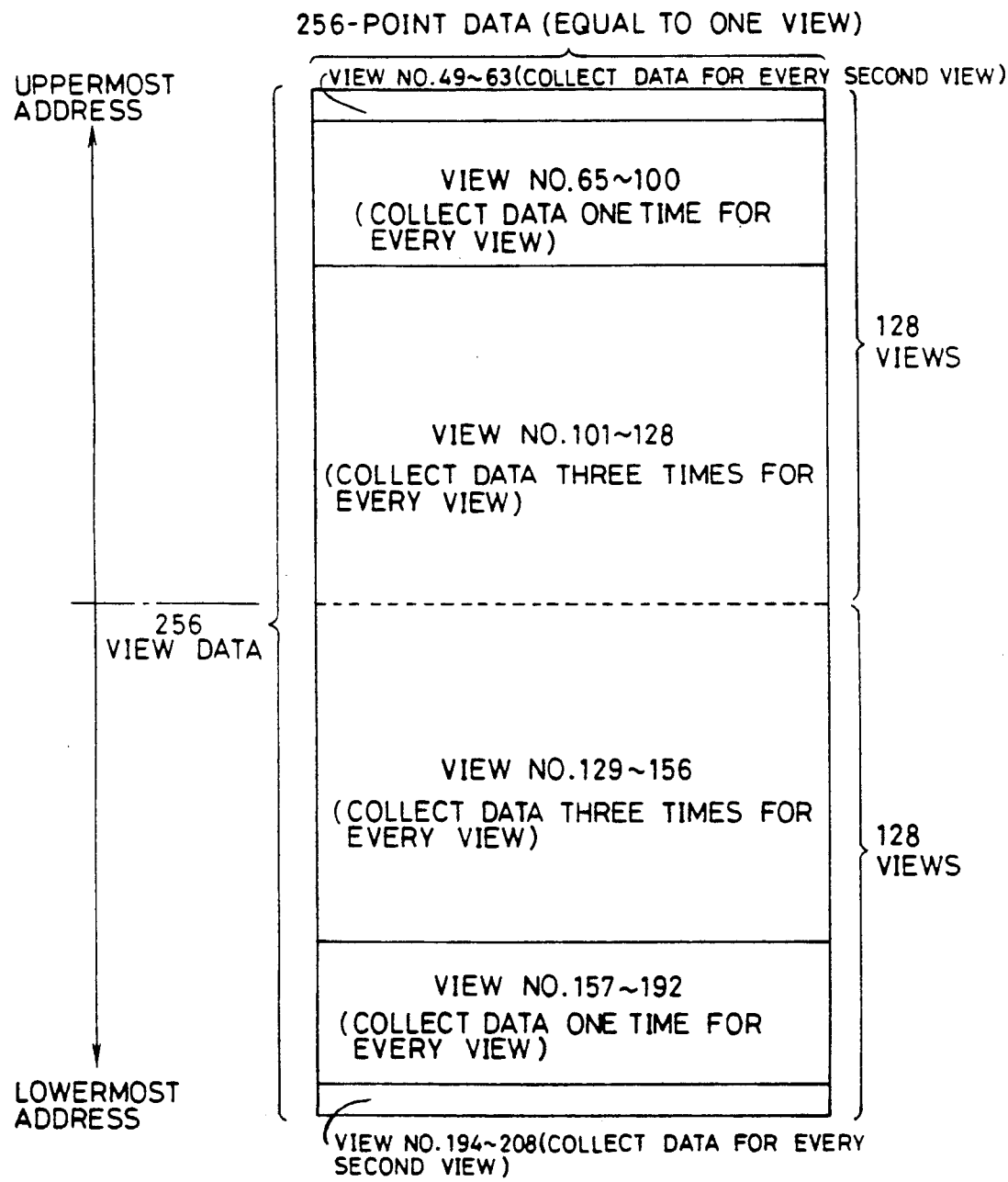
FIG. 10 is a diagram to illustrate the memory layout in which the collection of data is to be stored in the array processor memory shown in FIG. 7.

All the data collected by the data collection circuit 5 will be mapped onto the memory 603 in the array processor 602 in the layout format as shown in FIG. 10. The memory 603 is logically divided into the two symmetrical sections along the line of the 128th view data, and the collected data is placed in these sections, beginning with the 128th line toward the uppermost address and toward the lowermost address. It may be appreciated that all data are evenly divided into two parts, and data processing may proceed in the same manner for both parts, beginning with the center line toward the uppermost address and toward the lowermost address.

When data processing occurs in the data processing circuit 6, the view data to be operated on is saved into the appropriate buffer area, and is then restored into the appropriate collected data save area shown in FIG. 10 after the operation for that view data is completed. In this way, space in the memory 603 can be saved. For more than a single adding operation, such as a triple adding operation, data that is equal to three views may be saved, and a summing and averaging operation may be performed for the three view data. The sum that results from that operation, which is equal to one view data, is placed back into the memory 603. This will free the data space in the memory 603 that is equal to two view data, and memory space can be saved.

Figure 11A:
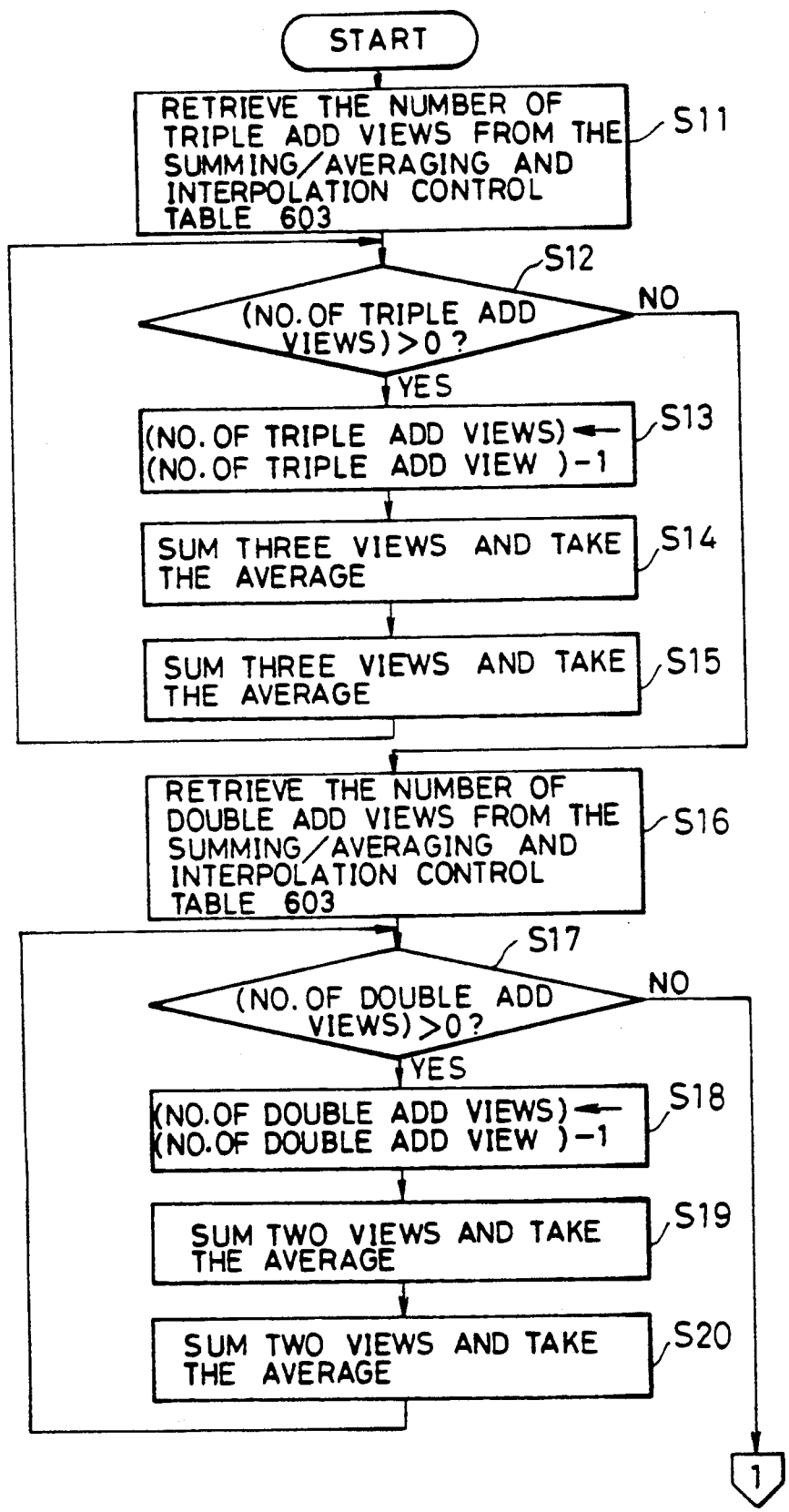
FIG. 11A, 11B, and 11C are flowcharts showing the steps in an example of the data processing procedure to be followed in performing the summing/averaging and interpolating operations.
Figure 11B:
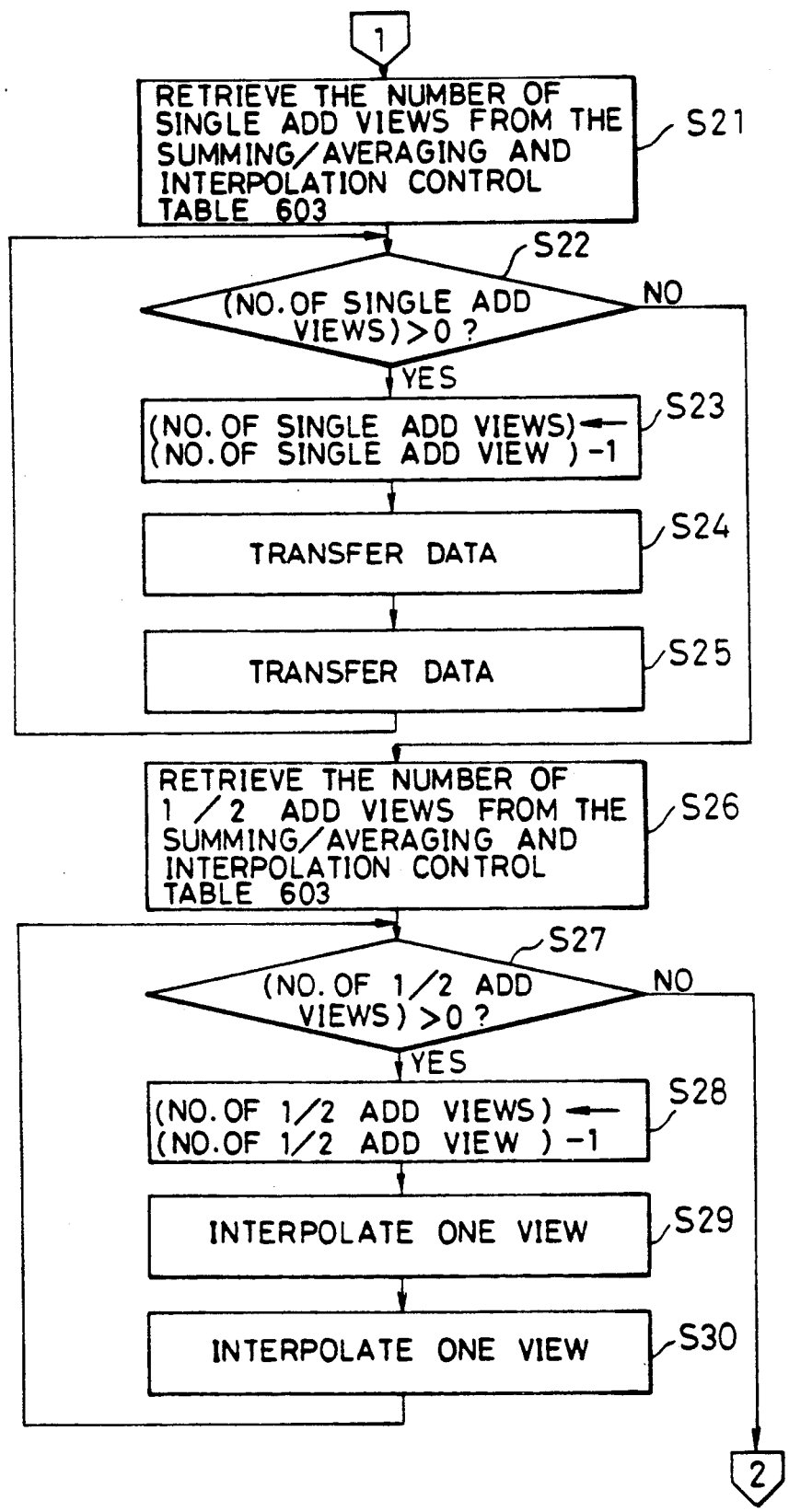
Figure 11C:
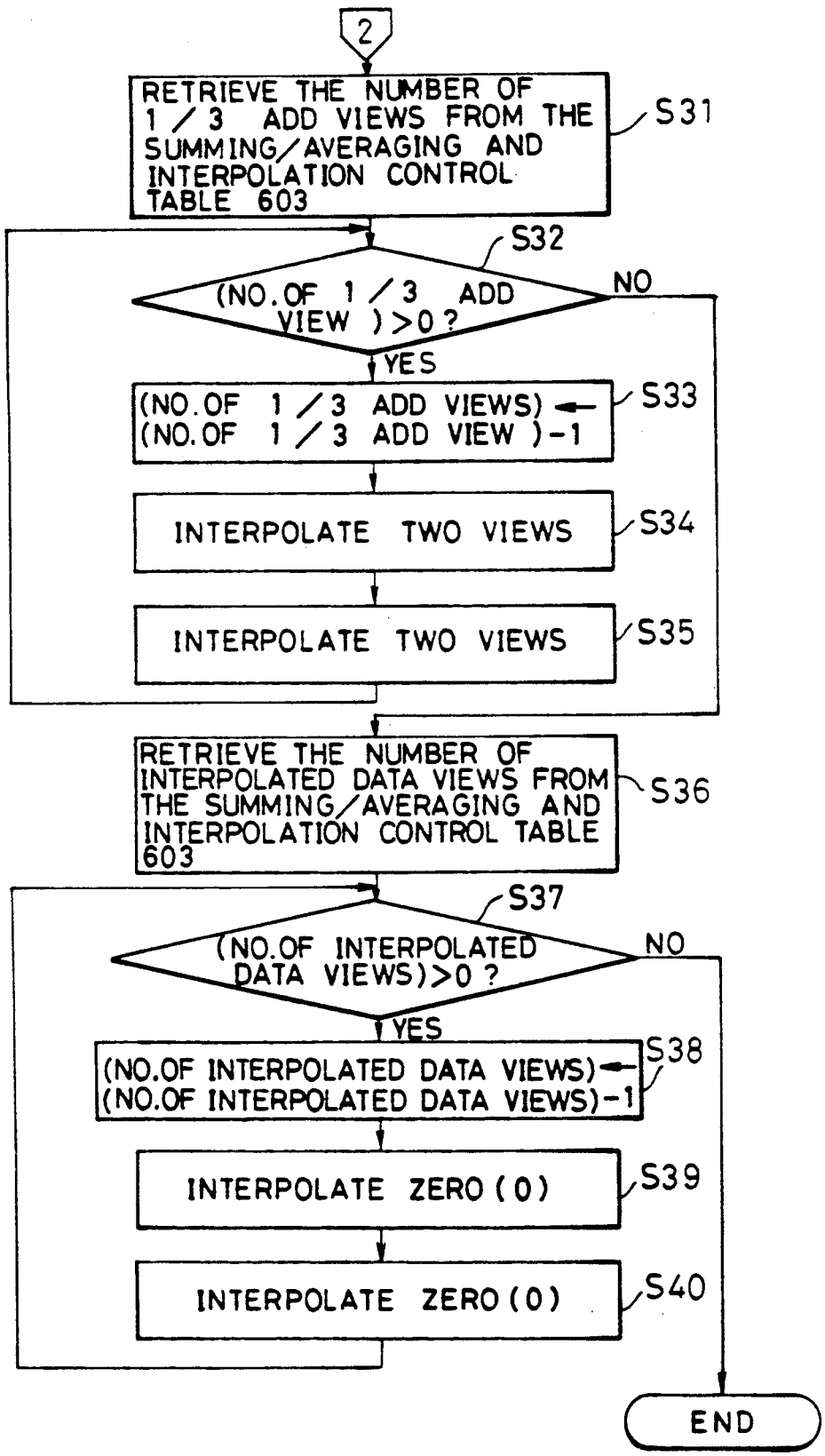

Referring next to FIGS. 11A, 11B and 11C, one example of the summing/averaging and interpolating procedure, which resides in the memory 604 in the array processor 602, is described.

At step S11, the number of the triple add views is retrieved from the summing/averaging and interpolation control table 603. At step S12, it is determined whether the number of the triple add views is greater than zero (0). It if is greater than zero, step S13 is taken, and if it is not greater than zero, the three view summing/averaging operation is skipped, going to step S16.

At step 13, the number of the triple add views is decremented by one (1). At the following step S14, the data of three views located, beginning with the center divisional line toward the uppermost address, is transferred to the buffer, and the summing and averaging operation is performed for that data. At step S15, the data of three views located, beginning with the center divisional line toward the lowermost address, is transferred to the buffer, and the summing and averaging operation is performed for that data. When the operation at step S15 is completed, control goes back to step S12.

The three view summing/averaging operation will be repeated until the number of the triple add views reaches zeros (0), when control goes to step S16 where the two view summing/averaging operation will be performed.

At step S16. the number of the double add views is retrieved from the summing/averaging and interpolation control table 603. At step S17, it is determined whether the number of the double add views is greater than zero (0). If it is greater than 0, step S18 is taken, and if it is not greater than 0, the two view summing/averaging operation will be skipped, going to step S21.

At step 18, the number of the double add views is decremented by one (1). At the following step S19, the data of two views located, beginning with the center divisional line toward the uppermost address, is transferred to the buffer, and the summing and averaging operation is performed for that data. At step S20, the data of two views located, beginning with the center divisional line toward the lowermost address, is transferred to the buffer, and the summing and averaging operation is performed for that data. When the operation at step S20 is completed, control goes back to step S17.

The two view summing/averaging operation will be repeated until the number of the triple add views reaches zero (0), when control goes to step S21 where the single view summing/averaging operation will be performed.

At step S21, the number of the single add views is retrieved from the summing/averaging and interpolation control table 603. At step S22, it is determined whether the number of the single add views is greater than zero (0). If it is greater than 0, step S23 is taken, and if it is not greater than 0, the single view summing operation will be skipped, going to step S26.

At step 23, the number of the single add views is decremented by one (1). At the following step S24, the data of single views located, beginning with the center divisional line toward the uppermost address, is transferred to the designated location. At step S25, the data of single views located, beginning with the center divisional line toward the lowermost address, is transferred to the designated location. When the operation at step S25 is completed, control goes back to step S22.

The single view summing operation will be repeated until the number of the single add views reaches zero (0), when control goes to step S26 where the single view interpolating operation will be performed.

At step S26, the number of the ½ add views is retrieved from the summing/averaging and interpolation control table 603. At step S27, it is determined whether the number of the ½ add views is greater than zero (0). If it is greater than 0, control goes to step S28, and if it is not greater than 0, the single view interpolating operation is skipped, going to step S31.

At step S28, the number of the ½ add views is decremented by one (1). At the following step S29, the data of two views located, beginning with the center divisional line toward the uppermost address, is transferred to the buffer, and linear interpolation is performed to generate one view between the two views.

At step S30, the data of two views located, beginning with the center divisional line toward the lowermost address, is transferred to the buffer, and linear interpolation is performed to generate one view between the two views. When the operation at step S30 is completed, control goes back to step S27.

The single view interpolation operation will be repeated until the number of the ½ add views reaches zero (0), when control goes to step S31 where the two view interpolation is performed.

At step S31, the number of the ⅛ add views is retrieved from the summing/averaging and interpolation control table 603. At step S32, it is determined whether the number of the ⅛ add views is greater than zero (0). If it is greater than 0, control goes to step S33, and if it is not greater than 0, the two view interpolating operation is skipped, going to step S36.

At step S33, the number of the ⅛ add views is decremented by one (1). At the following step S34, the data of two views located, beginning with the center divisional line toward the uppermost address, is transferred to the buffer, and linear interpolation is performed to generate two views between the two views.

At step S35, the data of two views located, beginning with the center divisional line toward the lowermost address, is transferred to the buffer, and linear interpolation is performed to generate two views between the two views. When the operation at step S35 is completed, control goes back to step S32.

The two view interpolation operation will be repeated until the number of the ⅛ add views reaches zero (0), when control goes to step S36 where the zero interpolation is performed.

At step S36, the number of the interpolated data views is retrieved from the summing/averaging and interpolation control table 603. At step 37, it is determined whether the number of the interpolated data views is greater than zero (0). If it is greater than 0, control goes to step S38, and if it is not greater than 0, the summing/averaging and interpolating operation will be terminated.

At step S38, the number of the interpolated data views is decremented by one (1). At the following step S39, the data of single views located, beginning with the center divisional line toward the uppermost address, is all assumed to be zero (0). At step S40, the data of single views located, beginning with the center divisional line toward the lowermost address is all assumed to be zero (0). When the operation at step S40 is completed, control goes back to step S37.

The zero interpolation operation will be repeated until the number of the interpolated data views reached zero (0), when the summing/averaging and interpolating operation will be terminated.

Subsequent to the steps described so far, the control computer 9 places the image reconstruct circuit 7 under its control, allowing it to perform the Fourier transform functions for the view data as corrected by the data processing circuit 6 and create the image data.

According to the present invention, part of the data collection may be suppressed for those views whose signal strengths are relatively small, and the data collection may occur several times under the same conditions for those views whose signal strengths are relatively great. For the views for which the data collection has been suppressed, interpolation may occur to generate data. For the views for which the data collection has occurred several times, a summing/averaging operation may be performed. The image can thus be created with an improved S/N ratio without increasing the time required for the data collection.

We claim:

1. In a magnetic resonance imaging apparatus for producing image data of an object being examined by subjecting the object to magnetic fields and RF pulse signals which produce echo signals, an arrangement comprising:

sensor means for detecting signals representing views of an object being examined, said signals being echo signals;

data collecting means for selectively performing a data collection process on said echo signals to produce collected data wherein for those ones of said echo signals of a relatively small strength, part of the data collection process is suppressed and wherein for those ones of said echo signals of a relatively great strength, the data collection process is performed a plurality of times under identical operating conditions;

data processing means for processing collected data to produce view data responsive to said data collecting means wherein for said echo signals for which the data collection process has been suppressed, interpolation data is produced and wherein for said echo signals for which the data collection process has been performed a plurality of times, a summing and averaging operation of times, a summing and collected data, said data processing means combining the interpolation data with the summed and averaged data thereby producing view data; and image constructing means responsive to the view data from said data processing means, for performing a Fourier transform on said view data thereby constructing image data.

2. The arrangement in a magnetic resonance imaging apparatus as defined in claim 1, wherein the imaging apparatus operates to vary a phase encoding gradient magnetic field a specific number of times and detects a corresponding number of echo signals, whereby for those echo signals whose phase encoded amount is relatively great, the data collection process is suppressed, and whereby for those echo signals whose phase encoded amount is relatively small, the data collection process is performed a plurality of times in the identical phase encoding gradient magnetic field.

3. The arrangement in a magnetic resonance imaging apparatus as defined in claim 2, further including memory means for pre-storing patterns used to vary said phase encoding gradient magnetic field.

4. The arrangement in a magnetic resonance imaging apparatus as defined in claim 1, wherein said data processing means includes memory means having two symmetrical sections divided along a center border thereof for storing all of said collected data collected by said data collecting means, said collected data being evenly divided between the two symmetrical sections, beginning with said center border toward an uppermost address in one of said sections and toward a lowermost address in the other section.

5. The arrangement in a magnetic resonance imaging apparatus as defined in claim 1, wherein said data collecting means comprises a scan controller.

6. The arrangement in a magnetic resonance imaging apparatus as defined in claim 1, wherein said data processing means comprises an array processor.

7. The arrangement in a magnetic resonance imaging apparatus as defined in claim 6, wherein said array processor includes data memory means having two symmetrical sections divided along a center border thereof for storing all of said collected data collected by said data collecting means, said collected data being evenly divided between the two symmetrical sections, beginning with said center border toward an uppermost address in one of said sections and toward a lowermost address in the other section.

8. A magnetic resonance imaging apparatus comprising:
   a static magnetic field coil for applying a static magnetic field in a main direction to a subject;
   a first gradient magnetic coil for generating a first gradient magnetic field to perform a frequency encoding on spins in the subject, said first gradient magnetic field being oriented in the main direction and changing in magnitude along a first direction perpendicular to the main direction so as to be superimposed on said static magnetic field;
   a second gradient magnetic coil for generating a second gradient magnetic field to perform a phase encoding on the spins in the subject, said second gradient magnetic field being oriented in the main direction and changing in magnitude along a second direction perpendicular to both the main and first directions so as to be superimposed on said static magnetic field;
   an RF transmit/receive coil for generating a 90° RF pulse to excite the spins in the subject, and a 180° RF pulse to produce echo signals from the excited spins, for each of a plurality of data acquisition cycles;
   sensor means for detecting the echo signals and for producing respective detection signals in response to the echo signals;
   data collecting means for converting said detection signals into digital echo data and for storing the digital echo data, in each of said data acquisition cycles, wherein said digital echo data is acquired over a plurality of data acquisition cycles, and the plurality of acquired digital echo data are divided into a first class of digital echo data and a second class of digital echo data, said first class of digital echo data being associated with echo signals having a strength less than a first predetermined value and being acquired and stored at a predetermined interval, and said second class of digital echo data being associated with echo signal having a strength greater than the first predetermined value and being repeatedly collected a plurality of times without changing the magnitude of the second gradient magnetic field;
   data processing means for generating interpolation data for the first class of digital echo data, and for performing a summing and averaging operation on the second class of digital echo data, to thereby produce view data; and
   image constructing means for performing Fourier transformation on said view data to produce image data.

9. The magnetic resonance imaging apparatus as claimed in claim 8, wherein:
   said data collecting means acquires at a predetermined interval detection signals having phase encoding magnitudes greater than a second predetermined value as the first class of digital echo data; and
   said data collecting means repeatedly collects the plurality of times detection signals having phase encoding magnitudes less than the second predetermined value as the second class of digital echo data while maintaining the magnitude of the phase encoding.

10. The magnetic resonance imaging apparatus as claimed in claim 9, further including memory means for pre-storing patterns for varying said second gradient magnetic field.

11. The magnetic resonance imaging apparatus as claimed in claim 8, wherein said data collecting means divides said digital echo data in accordance with the magnitude of the phase encoding performed by the field of said second gradient magnetic coil, and said data processing means includes memory means for storing said digital echo data symmetrically with regard to the middle of said memory means.

12. The magnetic resonance imaging apparatus as defined in claim 8, wherein said data collecting means comprises a scan controller.

13. The magnetic resonance imaging apparatus as defined in claim 8, wherein said data processing means comprises an array processor.

14. The magnetic resonance imaging apparatus as claimed in claim 13, wherein said data collecting means divides said digital echo data in accordance with the magnitude of the phase encoding performed by the field of said second gradient magnetic coil, and said array processor includes a data memory for storing said digital echo data symmetrically with regard to the middle of said data memory.

15. In a magnetic resonance imaging apparatus which subjects an object to magnetic field and RF pulse signals which produce echo signals, a method of producing image data of an object being examined, comprising:
   detecting echo signal representing views of an object being examined;
   producing collected data by selectively performing a data collection process on the detected echo signals, including suppressing part of the data collection process for echo signals of a relatively small strength, and performing the data collection process a plurality of times under identical operating conditions for echo signals of a relatively great strength;
   processing collected data to produce view data, including producing interpolation data for echo signals for which the data collection process has been suppressed, performing a summing and averaging operation on the collected data for echo signals for which the data collection process has been performed a plurality of times, and combining the interpolation data with the summed and averaged data to produce view data; and
   performing a Fourier transform on the view data to construct image data.

16. The method in a magnetic resonance imaging apparatus as defined in claim 15, further comprising:
   varying a phase encoding gradient magnetic field a specific number of times; and
   detecting a correspond number of echo signals;
   whereby, for echo signal whose phase encoded amount is relatively great, the data collection process is suppressed, and for echo signals whose phase encoded amount is relatively small, the data collection process is performed a plurality of times in the identical phase encoding gradient magnetic field.

17. The method in a magnetic resonance imaging apparatus as defined in claim 16, further comprising:
   pre-storing in memory patterns used to vary the phase encoding gradient magnetic field.

18. The method in a magnetic resonance imaging apparatus as defined in claim 15, further comprising:
   dividing the collected data into two equal parts; and
   storing the divided collected data symmetrically in memory along a center border thereof beginning with the center border of the memory toward an uppermost and a lowermost address, respectively.

* * * * *